United States Patent [19]

Rubinstein

[11] Patent Number: 4,971,760
[45] Date of Patent: * Nov. 20, 1990

[54] NOVEL METHOD FOR DISINFECTING RED BLOOD CELLS, BLOOD PLATELETS, BLOOD PLASMA, AND OPTICAL CORNEAS AND SCLERAE

[75] Inventor: Alan I. Rubinstein, Beverly Hills, Calif.

[73] Assignee: University of Southern California, Los Angeles, Calif.

[*] Notice: The portion of the term of this patent subsequent to Jul. 31, 2007 has been disclaimed.

[21] Appl. No.: 230,839

[22] Filed: Aug. 9, 1988

Related U.S. Application Data

[63] Continuation-in-part of Ser. No. 892,058, Sep. 1, 1986, which is a continuation-in-part of Ser. No. 838,253, Mar. 10, 1986, abandoned.

[51] Int. Cl.$^5$ .......................... A61L 2/18; A61L 2/20; C07K 15/06
[52] U.S. Cl. ......................... 422/37; 422/28; 435/2; 514/833; 530/385
[58] Field of Search .................. 422/28, 37; 424/101, 424/52; 530/385; 435/2; 514/833

[56] References Cited

U.S. PATENT DOCUMENTS

| | | | |
|---|---|---|---|
| Re. 27,359 | 5/1972 | Ilg | 424/101 X |
| Re. 31,799 | 12/1984 | Alliger | 422/28 X |
| 1,556,120 | 10/1925 | Mills | 424/101 X |
| 2,134,679 | 11/1928 | Allen | 422/28 X |
| 2,897,123 | 7/1959 | Singher | |
| 3,031,378 | 4/1962 | Ishidate | |
| 3,041,242 | 6/1962 | Barr et al. | 424/101 |
| 3,100,737 | 8/1963 | Allerswald et al. | 424/101 |
| 4,084,747 | 4/1978 | Alliger | 422/28 X |
| 4,314,997 | 2/1982 | Shanbrom | 424/101 |
| 4,481,189 | 11/1984 | Prince | 424/101 |
| 4,632,980 | 12/1986 | Zee et al. | 424/101 X |

OTHER PUBLICATIONS

Gallo, et al., Science, vol. 224, 4 May 1984, pp. 500-3.
Sarin, et al., J. Clin. Immunology, vol. 4, No. 6, pp. 415-23.
Wong-Staal, et al., Nature, vol. 317, 3 Oct. 1985, pp. 395-402.
Sarin, et al., NE J. Medicine, 28 Nov. 1985, p. 1416.

Primary Examiner—Robert J. Warden
Assistant Examiner—Jill Johnston
Attorney, Agent, or Firm—Poms, Smith, Lande & Rose

[57] ABSTRACT

It is well known that the transfusion of human blood and blood constituents, or the transplantation of corneas and sclerae, carries a substantial risk of transmission of AIDS and many other diseases. This disclosure describes a method of disinfecting certain blood constituents—particularly the red cells, platelets and proteins—or disinfecting corneal and scleral tissues, to make them safer for human transfusion or transplantation, while respectively maintaining their biologic or optical function. A sterilizing solution is prepared from, e.g., a commercially available disinfectant (such as LD ® of Alcide Corporation) containing primarily lactic acid and sodium chlorite. Normal saline solution is used as diluent instead of distilled water. The blood constituent or cornea or sclera is exposed to the disinfectant for a time sufficient to inactivate or reduce the infectivity of disease agents. The normal-saline environment prevents or deters hemolysis of the red blood cells or damage to the corneal or scleral epithelium or endothelium, disruption of the platelets, or denaturation of the proteins. The blood cells or platelets (or both), or the cornea or sclera (or both) are then washed with normal saline solution until the disinfectant concentration is insignificant. Plasma proteins are precipitated out as with ammonium sulfate, resuspended and dialyzed to remove residual disinfectant and coagulant, and reconstituted. The blood constitutents or eye parts are then safe for human transfusion or transplantation.

34 Claims, No Drawings

NOVEL METHOD FOR DISINFECTING RED BLOOD CELLS, BLOOD PLATELETS, BLOOD PLASMA, AND OPTICAL CORNEAS AND SCLERAE

RELATED APPLICATIONS

This is a continuation-in-part of U.S. patent application Ser. No. 892,058, filed Sept. 1, 1986; which in turn was a continuation-in-part of Ser. No. 838,253, filed Mar. 10, 1986 now abandoned.

BACKGROUND

1. Field of the Invention

This invention relates generally to processing of certain body tissues used in therapy, diagnosis and research. Such tissues include blood substances used in transfusions, as well certain organs and organ parts used in transplants. Thus the invention relates generally to blood substances, and to optical corneas and sclerae.

The invention relates more particularly to disinfecting such tissues—i. e., to disinfecting certain blood constituents, and corneas and sclerae. My invention may possibly also have future application to other transplant tissues.

For the purposes of this document, including the appended claims, I hereby define the phrase "blood constituent" to mean red blood cells, or blood platelets, or blood plasma. I also define the phrase "cellular blood constituent" to mean red blood cells, or blood platelets, but not plasma, or plasma proteins.

I further hereby define the phrase "blood product" to mean one or more blood constituents either alone or in combination, and either with or without other blood constituents or other substances. Thus one example of a "blood product" is whole blood, and another example is blood plasma.

This processing is designed to inactivate or greatly reduce the infectivity of certain harmful substances or contaminants, thus rendering the blood constituents, organs, or other tissues safe for human beneficial use—whether therapeutic, diagnostic, or experimental. Such harmful substances include, but are not limited to, several blood-borne viruses and other microorganisms as discussed below.

2. Prior Art

Human and animal tissues, particularly human blood products and corneal and scleral tissue (which encompasses parts of corneas and sclerae, as well as whole corneas and sclerae), are supplied for transfusion and transplantation purposes very commonly. There has been no way, however, to guarantee the safety of such tissues for transfusion or transplantation.

Transfusion of human blood products—particularly the constituents mentioned above—carries a well-known risk of transmitting harmful substances. The same is true of cornea, sclera, and other organ or organ-component transplants.

For the purposes of this document, including the appended claims, I hereby define the phrase "harmful substance" to mean a virus or other agent that can cause a disease or other harm.

Of particular interest are viruses that appear to cause various forms of hepatitis, including the hepatitis B virus; the non-A, non-B hepatitis virus or viruses. Others of interest are cytomegalovirus and Epstein-Barr virus.

Also of great interest is the virus, or group of viruses, linked with the incurable and often fatal disease known as acquired immune deficiency syndrome or "AIDS."0 This is probably caused by a retrovirus or group of retroviruses previously denominated "HTLV-III" and other HTLV types—and more currently "HIV", "HIV-1," "HIV-2," "HIV-3" and "HIV-4." The most common cause of AIDS is thought to be HTLV-III, now usually called HIV-1.

Detection and isolation of such cytopathic retroviruses from patients with AIDS, and certain members of groups that are at high risk for AIDS, have been frequently reported. One such report appears in Science 224:500-03 (1984).

Such findings are corroborated by P. S. Savin et al. in an article entitled "Human T-Lymphotrophic Retroviruses in Adult T-cell Leukemia-Lymphoma and Acquired Immune Deficiency Syndrome," J. Clinical Immunol. 4:415-23 (1984). Yet another report is by F. Wong-Staal and R. C. Gallo, "Human T-Lymphotrophic Retroviruses," Nature 317:395-402 (1985).

While the hazard of hepatitis and AIDS transmission through transfusion of blood products has received great public attention, the analogous hazard of such transmission through transplantation of eye tissues is a much less familiar matter. Nevertheless there is a recognized possibility of at least AIDS virus transmission from corneal transplantation, according to CORNEAL SURGERY Theory, Technique and Tissue, F. S. Brightbill, ed., p. 53 (Mosby 1986).

Furthermore, contamination of corneas by bacteria and fungi is documented, id. at 52, even though antibacterial solutions are commonly used in pretransplant storage of corneas—generally within the nutrient medium that supports the corneas. Hence this field of surgery also has need for a more effective means of controlling bacterial and fungal invasion.

For purposes of biomedical research, analysis and therapy it is of course very important to understand and use all of the distinctions between different kinds of virus or viruses that cause or at least are linked with various forms of hepatitis and AIDS. For present purposes of this document, however, it would be cumbersome and unnecessary to carry this multiplicity of distinctions and alternatives throughout my discussion.

Accordingly, in the interest of conciseness, throughout the following parts of this document I shall use a more general terminology. I shall refer to the various hepatitis viruses in a more general way as simply "hepatitis virus," and to the HTLV or HIV series, or both, simply as "AIDS virus."

In doing so I do not mean to detract in the slightest from the importance of the distinctions and uncertainties associated with the various nomenclatures. Thus a hepatitis virus is a "harmful substance," as is an AIDS virus, and of course there are other such substances.

There is an important need to make human blood products, human corneas and sclerae, and other tissues used as transfusions and transplants safe from all such harmful substances. Until now, this critically urgent need has gone unmet.

I shall now discuss two different developments of roughly the last ten years which are relevant to my invention—but which heretofore have been unrelated to the problem of viral contamination of transfusions and transplants. The first of these is the development of new disinfectants that are capable of inactivating these viruses.

In particular, Sarin et al. have reported that a particular commercially available laboratory disinfectant can completely inactivate at least one form of AIDS virus. Sarin et al., however, make no mention or suggestion of applying the disinfectant to blood products or tissue transplants.

The disinfectant is composed of approximately 0.23 percent sodium chlorite and 1.26 percent lactic acid, and is marketed under the name LD ® by Alcide Corporation of Norwalk, Conn. The manufacturer directs that LD be diluted in distilled water before use. Sarin et al. reportedly used it at dilutions of 1:200 and 1:100 or less, in water, as they describe in New Engl. J. Med. 33:1416 (1985).

The subject disinfectant corresponds to a composition which is patented by Howard Alliger in U.S. Pat. No. Re. 31,779. According to his patent, he prefers sodium chlorite as a chlorine-dioxide-liberating material; but he suggests substitution of "other water-solubilizing cations"—e. g., other alkali metals such as potassium, and alkaline-earth metals.

Alliger also indicates that up to eighty-five percent of the lactic acid may be replaced by other acids, preferably with analogous structure. Organic acids expressly enumerated include acetic, citric, sorbic, fumaric and tannic; and inorganic acids mentioned include sulfuric, hydrochloric and phosphoric.

Alliger, as with Sarin et al., makes no mention or suggestion of applying the disinfectant to blood products for transfusion, or to corneal, scleral, or other tissues intended for transplant. To the contrary, he asserts that certain components—particularly the lactic acid—of the subject disinfectant impart to it an extraordinary natural affinity for the material of cell walls, and thus accessibility to the interiors of cells.

This property assertedly or apparently results in effective invasion of bacterial cells, with consequent bactericidal action—sometimes perhaps including lysis. If a suggestion were made to use such a disinfectant for the external portions of blood products or transplant tissues, then based upon Alliger's disclosure such a suggestion would probably be rejected—since one might expect the disinfectant to invade and injure blood cells, platelets, or transplant tissues too.

My invention relates to three types of tissues: cellular blood constituents, noncellular blood constituents or plasma, and eye components. At this point in the discussion it will be helpful to briefly discuss these three separately to clarify certain contrasts among them.

With respect to cellular blood constituents in particular, as far as I know, heretofore no disinfectant has been used or suggested. If such a suggestion were made, it would generally be discounted for two reasons.

First, in general disinfectants strong enough to significantly inactivate viruses would damage the cellular constituents. Secondly, with such a strong chemical, any residual disinfectant in the cellular constituents to be transfused could be hazardous to the recipient of the transfusion.

With respect to corneal and scleral tissue, as noted above, the most potent prophylactic substances now used are antibacterials, and even these apparently are of questionable efficacy. Hence it may be understood that in this delicate context even antibacterials must be relatively mild in their effects to be useful at all.

With respect to blood-plasma treatment, the situation is somewhat more complicated. Whereas in the case of cellular blood products no disinfectants have heretofore been known, and in the case of corneas only mild antibacterials have heretofore been known, in the case of plasma disinfection at least one potent disinfectant has been placed in commercial use.

That material is beta-propiolactone. In this field it is usually employed to disinfect plasma preliminary to fractionation. Such a process has been used for isolation of therapeutic immune globulin, Factor VIII and IX, and other proteins.

Beta-propiolactone, however, is a known carcinogen and hence potentially very dangerous. To the extent that significant residual quantities of this material may remain in the blood product which is actually transfused, the use of propiolactone may possibly represent a significant hazard.

The other relatively recent development which is relevant to my invention—but not previously connected effectively with disinfection of blood constituents—is the introduction of automated cell washers (e.g., the IBM Model 2292 Cell Washer). These devices can wash red blood cells or platelets, or coagulated plasma proteins.

Automated cell washers are programmable to put very large quantities of biological cells through a predetermined cycle of chemical exposures, rinses, spins, and so forth. The machines accomplish this with great precision and reliability on a high-volume production-line basis.

At the same time, however, they can be made to apply such procedural steps to cells while the cells are kept in individual relatively small discrete volumes—such as, in particular, the "units" in which blood donations are received—thereby avoiding various problems inherent in pooling of donations. Heretofore, however, cell washers have not played any role in ameliorating the problems of viral contamination discussed above.

Thus no process to eliminate or lessen transmission of harmful substances in transfusion of blood constituents, or in transplantation of organs or organ parts such as corneal and scleral tissue, has been available.

SUMMARY OF THE DISCLOSURE

Units of certain blood constituents—and potentially units of blood products such as whole blood—as well as transplant tissues such as corneas and sclera, can be safely and economically sterilized, with materials readily available. I have devised a method by which this can be accomplished quickly and easily.

For blood products, my method can be implemented even while the blood product is in a collection bag. For corneas and sclera (or parts thereof), the method can be implemented with only minor, nondisruptive departure from familiar surgical protocols.

As will be recalled, in this document I am using the term "blood constituent" to mean specifically red blood cells, platelets or plasma. As will also be recalled I am using the term "blood product" to mean any blood constituent, either isolated or in combination with other blood constituents.

The blood product may itself simply be such a constituent, or combination of constituents, isolated. Alternatively, the blood product may also include blood plasma or some other medium, as well as other materials that may or may not be of interest.

As previously defined for purposes of this document, a "harmful substance" may be hepatitis or AIDS virus, or cytomegalovirus or Epstein-Barr virus. I intend the phrase also to encompass various microorganisms sometimes found in blood, such as Trypanosoma cruzi—which has a high incidence in Central and South America—as well as other parasites. Indeed, it is possible for a "harmful substance" to be any one of a great number of other viruses, or other microorganisms.

This last statement is of course a sweeping one, but as will be seen it is entirely justified because the method of my invention can be used with a very powerful disinfectant. In fact my method can be used with a disinfectant that is strong enough to inactivate extremely hardy viruses and other agents, such as the AIDS virus.

Accordingly it may be considered likely or probable that the method of my invention can be used to inactivate virtually any virus or virus-like agent of biomedical interest. A harmful substance may also be any or all of the above in combination.

Cellular blood constituents

A first embodiment of my invention is a method for treating a blood product comprising at least one cellular blood constituent, to inactivate or greatly reduce the activity of a harmful substance in that blood constituent.

This first embodiment of my invention itself includes at least three steps. The first step is adding disinfectant to the cellular-constituent-containing blood product.

The second step, which is performed after the first, is separating the disinfectant from the one or more cellular constituents of interest—that is, from the red blood cells, platelets, or combinations thereof. The third step, performed after the second, is providing the one or more cellular blood constituents for a beneficial use.

Some preferred forms of my invention as considered broadly will be mentioned below. At this point, however, I shall preliminarily mention one point that is of particular interest when the constituent of interest is cellular.

In this case I prefer to carry out the separating step by washing the constituent in an automated or semiautomated cell washer. This washing should be pursued until the concentration of disinfectant is reduced to an insignificant level.

Blood products generally, including plasma

A second embodiment of my invention is a method for reducing the infectivity of a virus, to prepare a blood product for beneficial use. Thus this embodiment, unlike the first, is not limited to blood constituents that are cellular.

This second embodiment of my invention includes at least four steps. The first step includes selecting or preparing a disinfectant that comprises (1) an organic acid, (2) a compound that when dissolved provides a water-solubilizing cation, and (3) a diluent medium that renders the disinfectant substantially isotonic with blood. Some of this terminology will be clarified by example shortly.

The second step includes exposing a blood product, comprising at least one blood constituent selected from the group consisting of red blood cells, platelets and plasma, to the disinfectant for a time period sufficient to inactivate any of such virus that may be present.

The third step, which is performed after the first two, includes separating the disinfectant from the blood constituent. The fourth step, which follows the third, includes providing the blood constituent for a beneficial use—as defined earlier for cellular constituents.

Once again, certain refinements will be mentioned below that relate to all embodiments of my invention as conceptualized broadly and generally, but some will be mentioned here that are of particular significance when the constituent of interest includes the blood plasma, and the proteins in it.

In this case, the separating step advantageously includes precipitating out the plasma proteins in a generally conventional fashion, but taking particular care to remove all of the disinfectant and other substances present. Preferably this precipitation is produced by contact with ammonium sulfate or like precipitating agent, generally at a concentration of eighty percent or less.

The next substep after precipitation is resuspension of the proteins in a relatively small volume of normal saline, followed by exhaustive dialysis against a relatively large volume of normal saline. This dialysis serves to separate the proteins from the disinfectant, and from the precipitating agent (e. g., ammonium sulfate) and the blood-isotonic diluent, as well as other substances that may be present.

Dialysis, as is common knowledge in the field of blood-product treatment, operates by means of the osmotic differentiation at a semipermeable membrane. It should generally proceed for up to two full days. The dialysis substep effectively reduces the concentration of disinfectant (as well as precipitating agent, salt, etc.) to a negligible level.

If preferred, the dialysis substep may be replaced by high-speed centrifugation. The latter should be followed by discarding of the supernatant, and then washing; and the process may be iterated as appropriate.

Next the proteins may be reconstituted in normal saline, preparatory to the providing step.

Corneas or sclerae

This third embodiment of my invention is a method for treating corneal or scleral tissue, to inactivate or greatly reduce the activity of a virus in the tissue. This method includes at least four steps.

The first is selecting or preparing a disinfectant that comprises (1) a disinfecting substance that is capable of inactivating or greatly reducing the activity of such a virus, and (2) a substance that deters damage of the cornea by the disinfecting substance.

The second step is exposing the cornea or sclera (or part) to the disinfectant. As with the previously discussed embodiments, this second step may be made to overlap with the first in any of myriad variations—all within the scope of my invention.

The third step, which follows the first two, is separating the disinfectant from the corneal or scleral tissue. The fourth step, which is performed after the third, is providing the tissue for use as a corneal or scleral transplant.

Specific to this embodiment of the invention for corneas and sclerae, the third step includes immersing and rinsing the tissue in normal saline. It also includes maintaining that immersion and rinsing, with agitation if desired, until no detectable concentration of disinfectant remains with the tissue.

Preferred forms of the invention generally

In discussing three embodiments of my invention above I have referred to "beneficial use." Probably the most prevalent form of such use will be therapeutic use. My invention is not limited, however, to that form of beneficial use, as it also encompasses diagnostic and even research or experimental uses.

The foregoing may be a description of three embodiments of my invention in their most general or broadest forms. As will be appreciated, however, for maximum enjoyment of the benefits of my invention I prefer to practice the method with certain advantageous detailed steps not mentioned above.

For example, before or in conjunction with the exposing step of the first-mentioned embodiment (relating to cellular blood constituents), I prefer to select or prepare a disinfectant that comprises a disinfecting substance and a substance that deters hemolysis. It is this disinfectant that is used in the exposing step.

I also prefer, in the selecting or preparing step, to select or prepare a disinfectant that is very generally isotonic with blood. This in turn I prefer to do by using as the substance that deters hemolysis a substance that is substantially isotonic with blood.

(While I regard these two preferences as refinements of the first-mentioned embodiment of my invention, they also will be recognized as integral parts of the second and third embodiments already discussed above. Thus the present discussion relates to all three embodiments.)

One such blood-isotonic substance that is very readily available is normal saline solution—0.9% of common salt, sodium chloride, in water. Another is 5% glucose solution, also in water.

I prefer to use normal saline as the diluent, and sodium chlorite and lactic acid as the disinfectant.

Chemically it is understood that the sodium chlorite in this material—perhaps through an intermediary stage involving chlorous acid—releases chlorine dioxide in water. It is probable that my substitution of normal saline for water does not interfere with the generation of chlorine dioxide.

In fact, the contribution of additional free chlorine ions from the saline solution may possibly enhance the environment for operation of the disinfectant. If so, my disinfectant-and-diluent combination therefore may possibly be superior in disinfecting power, as well as in hemolysis deterrence, to the manufacturer's recommended combination that uses water alone as diluent.

Such a disinfectant boost, if it does occur, may accordingly represent an added benefit of the use of normal saline as diluent in my invention. The same dual benefit may also possibly be available through other combinations of disinfectant and blood-isotonic diluent, which operate on the same principle proposed above.

In other words, other combinations—like the combination of lactic acid, sodium chlorite and normal saline described above—also may be internally complementary in developing an ionic population.

As previously mentioned, the Alliger patent Re. No. 31,779 suggests various substitutions for Alliger's preferred type of chlorine-dioxide-liberating material (sodium chlorite) and for all but fifteen percent of the preferred acid (lactic acid). In my opinion, for the present context of inactivating viruses in blood cells, platelets, and corneal and scleral tissue, the minor fraction of lactic acid will be found unnecessary. A limited amount of straightforward trial-and-error testing should suffice to explore this proposition. The essence of my invention is independent of whether it can be successfully practiced with less than fifteen percent of the acid being lactic acid.

Many otherwise equivalent diluents, however, particularly those compounds which produce an osmotic effect equivalent to that of normal saline, are available.

In particular, common salt is a salt of an alkali metal and a halogen; thus many other alkali-metal-and-halogen salts, and even more generally metal-and-halogen salts, will suggest themselves readily to those skilled in the art. Such salts include salts of other alkali metals such as calcium, potassium, and other metals generally such as magnesium; as well as salts made of other halogens such as fluorine and iodine.

Hence calcium fluoride, potassium chloride, magnesium bromide and so forth are all likely candidates—subject, of course, to their compatibility with the blood constituents to be disinfected. Any candidate equivalents must also be evaluated as to their amenability to the separating step that follows.

The treated tissues may also in some unusual instances retain some small residual of the disinfectant. Such retention is not desirable, and in the proper practice of my invention should be carefully avoided—as set forth at various other points in this document.

Nevertheless, a risk remains that trace quantities may remain. Against the possibility of such occurrence it is accordingly useful to evaluate candidate disinfectant-and-diluent combinations for their compatibility with the human bloodstream after transfusion. For example, trace quantities of lactic acid and sodium chlorite—are relatively nontoxic in comparison with beta-propiolactone and other proposed sterilants.

It will be understood, however, that these preferred forms of my invention are not limited to the use of metal-and-halogen salts as the blood-isotonic substance; but rather encompass the use of a wide range of other substances that are within the skill of chemical artisans to employ. Thus I do not mean for my claims to be circumvented by the mere substitution of other substances that are isotonic with blood, relatively harmless in residual quantities, and effective in combination with particularly complementary disinfecting components.

It must also be emphasized that the selecting or preparing step of my invention may proceed by assembling the various chemical ingredients in any of a great number of different orders. Thus, for example, in one arrangement that may be particularly attractive for commercial distribution purposes, salt may be premixed with disinfectant for commercial packaging, and this premixture then diluted with, for example, distilled (or otherwise sterile) water at the point of use.

The primary controlling consideration in these various possible sequences is that upon addition of diluent water the resulting mixture is substantially isotonic with blood. Aside from considerations of commercial practicality, the particular sequence employed is by-and-large immaterial to the practice of this preferred form of my invention.

In other words, premixed saline solution may be added to disinfectant, or salt may be premixed with disinfectant and water added later, or some of the salt may be premixed with the disinfectant and some with the water. The choice is not likely to matter, with these provisos:

First, as already stated, the mixture must be substantially isotonic with blood (or, what is usually in essence the same thing, substantially isotonic with the tissue to be disinfected). Secondly, the correct proportions must eventually be reached—generally before the exposing step, although as explained below the preparing and exposing steps may overlap to some extent. Thirdly, if the salt and disinfectant are premixed, the salt must be compatible with the disinfectant in the absence of the water.

Somewhat more generally, the preferred forms of my invention may comprise:

(1) diluting a disinfecting substance in a substance that is substantially isotonic with blood; or
(2) diluting a hemolyis-deterrent-containing substance in water; or
(3) both of the above.

Furthermore, although it is perhaps most natural and reliable to perform the exposing step after the selecting-or-preparing step, the two steps can instead be made to overlap in various ways, all encompassed within my invention.

For example, one may first place the tissue (blood product or transplant tissue) in the diluent medium, and then add the organic acid and cation-providing compound together to the tissue and diluent. This is advantageously done while mixing to avoid exposing any small part of the tissue to a high concentration of the acid and compound. Still again, one may:

first place the tissue in some of the diluent medium, and then add the rest of the diluent with the acid and the cation-providing compound; or first place the blood product in a mixture of the diluent medium and acid, and then add the cation-providing compound; or first place the blood product in a mixture of the diluent medium and cation-providing compound, and then add the acid; or proceed in any of a variety of combinations of these sequences that will now be clear to those skilled in the art of biochemical processing.

In short, the preparation of a mixture of disinfectant and hemolysis-deterrent-containing substance can be integrated into the process of body-tissue exposure. Thus, in effect, the mixture of disinfectant and hemolysis-deterrent-containing substance can be built up around the body tissue to be transfused or transplanted, if preferred, rather than first completing the mixture and then immersing the tissue in that mixture.

Dilution of disinfectant such as "LD" with normal saline may be between 1:2 and 1:2000. Advantageously the exposing step includes putting the disinfectant into an automated or semiautomated machine such as an IBM cell washer.

In addition it is preferable, between the exposing step and the separating step, to maintain the disinfectant in contact with the tissue for an extended time period. By "extended" I mean a period of at least five seconds; however, under ordinary laboratory conditions the time need not exceed thirty minutes.

As a practical matter I prefer to use a "maintaining" time period between approximately one and seven minutes. This contact period appears sufficient to obtain the advantages of the invention without needless delay.

It will be understood, however, that the time may be adjusted in accordance with well-known principles of chemistry to accommodate treatment of the tissue while it is refrigerated, or even while it is heated. Again, care must be taken in using such lower or higher temperatures to avoid damage to the tissue from the temperature exposure itself—or from the combination of conditions of temperature and disinfecting substance.

I prefer to shake or otherwise agitate the tissue together with the disinfectant during the maintaining step. This technique enhances, and also somewhat hastens, completion of the reaction.

Generally for blood products, though of most importance in relation to cellular blood constituents, I prefer to carry out the separating step by washing the blood product in an automated or semiautomated cell washer. This washing should be pursued until the concentration of disinfectant is reduced to an insignificant level.

My procedure is practical, useful, easy, and economical. Its advantages particularly include eliminating, or at the very least strongly reducing, transmission of the previously mentioned harmful substances in blood transfusions and tissue transplants.

In particular, through use of diluent normal saline or equivalents it is possible to prevent or strongly deter hemolysis and thereby render my process invention noninjurious to the tissues.

In particular, I have verified that my process leaves substantially intact certain substances that are present in blood and are recognized as indicators of normal or healthy blood-constituent activity. These verifications will be described in a later section of this document. In short, the method of my invention disinfects blood constituents without damaging them.

In the foregoing discussion and other portions of this document I have used as a verbal shorthand the term "tissue" to refer both to blood constituents intended for transfusion and to corneas, sclerae or other tissues intended for transplantation. I mean this usage only for brevity and I do not mean to be misunderstood as suggesting that the various embodiments of my invention are identical or equivalent, or subsumed any one within any other.

All of the foregoing operational principles and advantages of the present invention will be more fully appreciated upon consideration of the following detailed discussion.

DETAILED DISCUSSION OF THE PREFERRED EMBODIMENTS

1. STERILIZATION TECHNIQUE

In a preferred form of my invention, I disinfect certain constituents of human blood as follows. First, if desired, the cellular blood constituents may be separated from the plasma and from plasma fractions or proteins such as coagulating factors, globulins and so forth.

If this is not done, however, there is no effect on the particular constituents of interest. At most only the unseparated plasma and its fractions will be discarded. Moreover, with the refinements of my invention described herein, it is possible to preserve the other fractions (with or without disinfecting them) through the disinfection process.

Next the blood product containing the constituents of interest is exposed for an extended period of time to a disinfectant solution. The meaning of this phrase "extended period of time" has been set forth above. The solution may be prepared in any of a great range of concentrations and in a variety of ways.

For example, the solution may be prepared following the various approaches suggested in the Sarin paper or Alliger patent discussed earlier, or in the instructions on the product label of the commercial disinfectant LD ®. These approaches or instructions, however, must be modified in accordance with my invention by substituting a blood-isotonic diluent for the distilled-water diluent specified elsewhere.

Thus for example the disinfectant solution may be composed, at a first-stage 1:10 dilution, of approximately 0.23 percent sodium chlorite and 1.26 percent lactic acid, diluted with normal saline (that is, a 0.9-percent aqueous solution of sodium chloride) by a second-stage 1:100 dilution—for a total of up to 1:200 or higher.

Alternatively for example the solution may possibly be usable at a 1:10 dilution, with appropriate adjustment of exposure time. For some purposes, however, this strength may be excessive or unnecessary. It appears that dilutions over as broad a range as 1:2 to 1:2000 may be usefully encompassed within my invention, although as already stated I prefer 1:100 to 1:200.

In standard procedure for collection and storage of red blood cells, the cells are first separated by centrifugation and then may be washed in normal saline solution. Since in such a procedure the cells may be in saline already, one convenient way of practicing my invention for red blood cells may be to simply add the disinfectant solution in a relatively concentrated form to the mixture of red cells and saline as washing begins, or after washing is complete but before the saline is removed.

Such addition should be performed gradually, and while the red cells and saline solution are mixed. These precautions should be adequate to minimize exposure of any small portion of the cells to a large quantity of the stronger disinfectant.

Another possibility for red blood cells is to follow the usual washing procedure, except for the substitution of the disinfectant-and-saline solution for saline alone. In either event, the disinfection can be performed either while the cells are in their original collection bag, or in a larger bag or other container.

My preference is to use a larger bag, so that the volume of disinfectant is less than half that of the bag, and the total volume of disinfectant and cells is substantially less than the total volume of the bag. My point here is simply to allow ample excess volume for thorough and effective mixing, so that none of the cells is overexposed and all are adequately exposed to the disinfectant.

Platelets, by contrast, are not usually washed in the present standard procedures for blood treatment. For present purposes, however, they are advantageously washed using any of the procedures described above for red blood cells.

Procedures for treatment and segregation of plasma proteins have been set forth above. General procedures for treatment of corneal and scleral tissue have also been outlined, but as will be understood the disinfection arrangements must be accommodated to the special needs and circumstances of the harvesting, nutritive and surgical environment.

Following exposure of the blood product to the disinfectant, the disinfectant is removed from the subject constituent. Such removal advantageously includes washing, with or without the aid of automation.

An automated cell washer (such as an IBM 2292 Cell Washer) may be used to particular advantage for red blood cells or for platelets. The washer may be programmed to give the disinfectant a 200-fold dilution of its standard-use dilution.

The washer may further be programmed to next mix the disinfectant with the constituent for a few seconds, or preferably for a few minutes. The washer may also be programmed to then wash the constituent automatically.

Automation increases the utility of my invention, since through the use of automation red blood cells, platelets, and even plasma proteins may be washed rapidly and the invention practiced on a production scale. Disinfectant composition, as well as disinfection times, may be varied without departing from the scope and spirit of my invention.

More specifically, disinfectant solution of sodium chlorite and lactic acid may be obtained from Alcide Corporation under the trademark LD ®. This material is provided commercially in two parts, a "base" and an "activator." These materials are understood to include sodium chlorite and lactic acid.

The two parts are mixed with diluent in accordance with the manufacturer's instructions, with one crucial exception: normal saline is substituted for the distilled water specified by the manufacturer. Thus, one part LD base is mixed with ten parts normal saline. One part activator is added and the solution further diluted with normal saline to an overall dilution of 1:200.

In the final disinfectant solution the concentrations of sodium chlorite and lactic acid are each below one percent. The pH of the solution is preferably adjusted to a value between four and six.

2. TISSUE SURVIVAL GENERALLY

I have determined that a blood constituent treated with this solution survives the treatment, intact and active.

This determination is not in the least self evident, for two general reasons already mentioned in the "Background" portion of this document. First, as far as I know, no suggestion has been made heretofore of applying the above-mentioned disinfectant in any form to body tissues for transfusion or transplantation.

Secondly, the cell-invasive capabilities of the patented disinfectant "LD" would lead a skilled person to expect invasion of blood-product or transplant-tissue cells, with concomitant damage. As a matter of fact, this concern is borne out in practice, if the subject disinfectant is prepared according to the manufacturer's directions (or as described by Sarin et al.).

Specifically, if the disinfectant is so prepared and then applied to human red blood cells, hemolysis results; if applied to platelets, disruption of the platelets will result. Both these results have been verified directly by experiment.

If "LD" disinfectant were similarly prepared and applied to corneal, scleral, and like delicate tissues, damage to at least the endothelium would result. In the case of corneal tissue, whose clear transmission and refraction of light are of course central to its function, even surface damage would typically render the entire corneal tissue useless.

Similarly, as far as I know, application of the above-discussed LD ® disinfectant to plasma has not been heretofore suggested. If, however, that disinfectant were prepared according to the manufacturer's directions and applied to plasma, denaturation of the plasma proteins would result.

It will be understood that the most-often transfused constituent of the three under discussion is the red blood cells. Hence it is most crucial to show that the usefulness of these cells persists after treatment, and my first experimentation accordingly was directed to such cells.

3. RED-BLOOD-CELL SURVIVAL

Two aliquots of red blood cells from a unit of red blood cells supplied by the American Red Cross were washed three times in normal saline. One of these aliquots was held in a container labeled "EXP" (experiment).

To this container, which was approximately one-third full, was added the above-described disinfectant in an amount to fill the container. The contents of the container were mixed, and the mixture allowed to stand for approximately ten to fifty seconds.

Then the cells were washed in normal saline four times and resuspended in normal saline. The disinfected cells were carefully inspected visually, and seen to be free of any visual indication of hemolysis.

The control aliquot of red blood cells was washed in identical fashion—that is to say, in normal saline—but no disinfectant was added. The control, too, was free from hemolysis.

To verify more fully that the red blood cells treated with the disinfectant were still viable and thus suitable for transfusion, assays were performed on them as described below. As detailed therein, the oxygen transfer capability and enzymatic activity of two representative constituents of the disinfected red blood cells were found to be substantially intact.

Based upon these several tests, I believe that the integrity of my process is established. After washing in normal saline, the red blood cells are ready for transfusion—safe from transmitting the various harmful substances mentioned earlier, and others.

The disinfected and washed cells were stored in normal saline for several days at approximately four degrees Celsius, followed by incubation at thirty-seven degrees Celsius in a solution of glucose, inorganic phosphorus, potassium, and magnesium.

The cells were then assayed for 2,3 DPG and ATP. The methodology used in these assays has been described. See, for example, A. S. Keith, "Reduced nicotinamide ademine denucleotide-linked analysis of 2,3 diphosphoglyceric acid: spectrophotometric and fluorometric procedures," *General Lab. Clin. Med.* 77:470 (1971). See also Worek, Gruber and Bergmeyer, "Adenosine, 5', triphosphate, determination with 3-phosphoglycerate kinase," in H. U. Bergmeyer's *Methods of Enzymatic Analysis* 4:2097, N.Y. Academic Press (1974).

The presence of 2,3-diphosphoglyceric acid (DPG) phosphatase activity in preparations of monophosphoglycerate mutase (PGM) from muscle and other sources has been noted by several workers. Lowry and coworkers exploited this presence to measure the very low levels of 2,3-DPG in acid extracts of brain tissue.

They measured a product of the phosphatase activity, 3-phosphoglyceric acid (3-PGA), fluorometrically. Lowry's group used a reduced nicotinamide adenine dinucleotide (NADH)-linked reaction.

In that reaction 3-PGA was converted stoichiometrically to glyceraldehyde 3-phosphate (G-3P) by phosphoglycerate kinase (PGK) and glyceraldehyde 3-phosphate dehydrogenase (G3PD). I have modified this fluorometric procedure for measurement of the much higher concentrations of 2,3-DPG in red blood cells.

Rose has reported that in red blood cells 2,3-DPG phosphatase is stimulated by both pyrophosphate and 2-phosphoglycolic acid, a property shared by phosphatase activity in muscle PGM. She has devised a spectrophotometric assay for 2,3-DPG with the use of 2-phosphoglycolate and PGM, converting the 3-PGA formed to lactate.

The fluorometric and spectrophotometric assays for 2,3-DPG described here are those which proved most versatile and reliable. They represent a composite of the methods of Lowry and coworkers, Rose and Liebowitz, and Czok and Eckert.

Materials and Methods

Imidazole (grade III), reduced glutathione (GSH), hydrazine sulfate solution (No. 750-3), and 2-phosphoglycolate were obtained. Distilled water was passed through a mixed-bed deionizer, which greatly reduced the fluorescence of the water.

Preparation of samples: Customarily, one volume of whole blood is added to two volumes of ice-cold six percent (w/v) perchloric acid (PCA); it is mixed thoroughly and left on ice for at least fifteen minutes. The brown, denatured protein is separated by centrifugation at 27,000 gravities for twenty minutes at two degrees Celsius. The clear supernatant is then neutralized with approximately one sixth volume of 2M $KHCO_2$.

Spectrophotometric assay: All reagents are prepared as stock solutions and stored frozen, except imidazole and hydrazine, which are stored at room temperature. Reactions are performed at twenty-five to twenty-eight degrees Celsius (without temperature control) in an automatic recording spectrophotometer in quartz semimicrocuvettes with one centimeter path lengths at 340 millimicrons.

For normal whole blood, neutral PCA extract (one-tenth milliliter) is added to one-milliliter aliquots of the reaction mixture. The volume of extract can be increased to at least three-tenths milliliter without affecting the reaction mixture.

The combined solution of G3PD and PGK (in four microliters) is added after all the 3-PGA and 1,3-DPG has reacted (usually they are undetectable), the absorbance at 340 millimicrons is determined at PGM (in five microliters) is added. The reaction normally goes to completion in fifteen to twenty minutes—but this should be determined for each new set of reagents, as the phosphatase activity of different lots of PGM varies slightly.

The blank cuvette contains distilled water instead of PCA extract. Blanks containing PCA extract, but no enzymes, are usually identical, but this should be verified periodically. When 2-mercapethanol was substituted for GSH, sporadically high blanks (0.03 to 0.04 O.D. units per ten minutes) were noted in the presence of neutral PCA extracts of whole blood without any added enzymes.

Fluorometric assay: A sample size of PCA extract (two to five microliters) is employed depending on the hematocrit of the sample. Samples and standards are added with the same selected micropipette. The reaction is complete in five minutes.

Calculations: 2,3-DPG concentration is derived by determining the difference in absorbance at 340 millimicrons before and after adding PGM, using an extinction coefficient of 6.22 O.D. units per millimole of NADH. The value is corrected for the reagent blank (usually less than 0.010 O.D. units). In the fluorometric assay, the change in NADH fluorescence is compared with that of a 2,3 Def solution which has been standardized spectrophotometrically.

There is a significant deviation from linearity in the absence of hydrazine when the initial concentration of 2,3-DPG approaches that of the available NADH. The obligatory liberation of inorganic phosphate from 2,3-DPG adversely affects the final ratio of 1,3-DPG to G-3-P so that G-3-P must be trapped with hydrazine, unless a large excess of NADH is employed.

Potency of the hydrazine solution should be verified periodically. This can be done by checking linearity against a standard curve.

The half-time of the fluorometric assay is normally less than one minute. Because of its great sensitivity, such an assay is readily used to measure very low concentrations of 2,3-DPG, such as might occur during storage of blood or in vitro experiments. The accuracy of this method is determined largely by the quality of the micropipettes and the skill of the technician in handling them.

Specificity: Adding PGM to the system results in the conversion of both 2,3-DPG and 2-DPA to 3-PGA. In normal blood, the concentration of 2-PGA is 300 times less than that of 2,3-DPG; it can be ignored. Where these compounds are present in more nearly equal concentrations, however, as in most tissues, discrimination may be more important.

The assay can be modified so that an approximation of 2-PGA content can be obtained by adding PGM (five milligrams per milliliter) without phosphoglycolate after 3-PGA has reacted. Under these conditions, 2-PGA will be rapidly converted to 3-PGA, while 2,3-DPG will react very slowly.

Selective activation of the phosphatase with phosphoglycolate will then measure 2,3-DPG. This modification requires fluorometric measurements of NADH for sufficient sensitivity at the low levels of 2-PGA usually present in tissues.

Methodology Advantages

The advantages of this method are several. Its most important aspect is that it is an "endpoint" assay rather than a rate assay. The assay methods which relate 2,3-DPG concentration to its catalytic effect on the PGM reaction involve rate measurements, which are much more likely to be affected by minor variations in assay conditions.

"Rate" in these methods is often determined by an initial reading followed after one time interval by a single additional reading, and assuming linearity. Any deviations from linearity among different samples will therefore go undetected. Further, the calculations depend on a calibration curve for a standard of known purity.

The "endpoint" assay, on the other hand, may be read at any convenient time after going to completion, provided that the blank cuvette is read at a similar interval. The calculations are based on the molar extinction coefficient of NADH when determined spectrophotometrically, and thus they do not depend on a standard curve.

If greater sensitivity is required, the fluorometric assay can be used. No fractionation of the extracted material is required, as it is in the total phosphate and chromotrophic acid methods.

The specificity, although not absolute because of the coreaction of 2-PGA, is entirely adequate for most red-cell applications, in which the 2-PGA concentration is negligible. Selective activation of 2,3-PGA activity by phosphoglycolate after 2-PGA has reacted can improve the specificity of the assay.

The "backward" reaction to G-3-P is more versatile than the "forward" reaction to lactate. Concentrations of 3-PGA and 2-PGA are usually negligible compared with that of 2,3-DPG.

Pyruvate on the other hand, may accumulate significantly under certain experimental conditions, and the initial lactate dehydrogenase reaction may then exhaust much of the NADH. Furthermore, at very low concentrations of 2,3-DPG, the coreaction of 2-PGA concentration exceeds that of 2-PGA by a factor of five to ten in the intact cell.

Results

Following incubation, the ATP and 2,3-DPG of the disinfected red blood cells (experiment) were compared with those of the untreated cells. These two enzymes are considered important predictors of the viability and suitability for transfusion of red blood cells.

No important difference in their ability to regenerate ATP and 2,3-DPG appeared. Results are displayed in Tables I and II. Both tables present concentrations obtained after disinfection, washing, protracted regrigeration, and incubation for the particular times tabulated.

Washing was in normal saline, and refrigeration was at four degrees Celsius as mentioned above. Incubations were performed at thirty-seven degrees Celsius, with the supplementation of glucose, inorganic phosphorus, potassium, and magnesium.

The experiments represented in Tables I and II differed principally in length of exposure to the

TABLE I

Red blood cell constituent concentrations (micromoles per gram hemoglobin) after described treatment, including disinfection for less than one minute

| Incubation | Control | | Experiment | |
|---|---|---|---|---|
| time (hr.) | ATP | 2,3-DPG | ATP | 2,3-DPG |
| 0 | 0 | 0 | 0 | 0 |
| 2 | 1.79 | 0.96 | 1.34 | 2.89 |
| 4 | 1.19 | 0 | 1.34 | 0 |

TABLE II

Red blood cell constituent concentration (micromoles per gram hemoglobin) after described treatment, including disinfection for four minutes

| Incubation | ATP | |
|---|---|---|
| time (hr.) | Control | Experiment |
| 0 | 3.83 | 5.28 |
| 2 | 4.35 | 4.26 | disinfectant. Table I corresponds to the previously described disinfection period, less than one minute.

Table II data were taken following a disinfection period of four minutes—a stringent test of the ability of the cells to survive the disinfection step. Following four minutes of contact with the disinfectant, there was no evidence of hemolysis and no loss of ATP.

I therefore conclude that red blood cells and hence the other two less-often-transfused blood constituents are safe and suitable for human transfusion, following treatment as described herein. These constituents carry a much lower risk or total absence of risk of transmitting the harmful substances enumerated earlier, and others.

Following all the foregoing experiments, a further complete test was conducted independently in a different laboratory by another skilled worker. That confirmatory test proceeded as follows.

Fresh, peripheral blood was drawn from a healthy donor. The blood was immediately centrifuged to separate red blood cells from the plasma. The plasma was entirely drawn off, together with a small amount (approximately one-half milliliter) of red blood cells to assure that the remaining material was composed of fresh red blood cells only.

Two equal aliquots of red blood cells were prepared by this procedure. Each aliquot was placed into an equal volume of a respective disinfectant solution.

For this purpose two different disinfectant solutions were prepared. One of these was prepared in accordance with heretofore-known methods for preparation of disinfectant for different purposes, and the other in accordance with the present invention, as follows.

The solution comporting with heretofore-known methods was made by first preparing 15.1% lactic acid, one volume, added to ten volumes of sterile water; and to this adding a solution of 2.73% sodium chlorite in a volume equal to that of the lactic acid. This solution was incubated at room temperature for seventy-five minutes, after which the solution was diluted 1:20 in sterile water.

Concurrently the other disinfectant solution, comporting with the present invention, was prepared in exactly the same way except that normal (i. e., 0.9%) saline was substituted for the sterile water at both points.

The two aliquots of red blood cells, each in its respective disinfectant solution, were incubated for one minute at room temperature.

In the mixture containing the heretofore-known solution, immediate lysis of the cells was observed. That mixture was next centrifuged, and then inspected visually. Damaged cells as well as intact cells can be centrifuged out of such a mixture, but the two are dissimilar in appearance. No survival of cells at the bottom of the centrifugation tube could be seen.

In the mixture containing the present-invention solution, no lysis was observed. That mixture too was next centrifuged, and then inspected visually. The upper, aqueous layer showed no evidence of free hemoglobin, and the red blood cells themselves had moved to the bottom of the centrifuge tube, giving the appearance of intact cells. In addition, spectrophotometric measurement of this mixture revealed no free hemoglobin.

4. PLATELET SURVIVAL

Two solutions were prepared for exposure to platelets. One was a disinfectant solution, and the other consisted of saline solution only.

The disinfectant solution was prepared by mixing two milliliters of LD ® base with twenty milliliters of cold normal saline, and allowing the mixture to stand for at least one hour; and then adding two milliliters of LD ® activator—and finally adding 480 milliliters of normal saline.

Two test tubes were each half-filled with platelets from a single, common unit of platelets. The remaining half of one tube was then filled with the above-described disinfectant solution, and the remaining half of the other tube was then filled with saline solution.

Both tubes were next shaken and allowed to stand for three minutes, and then centrifuged at high speeds for a long time. The supernatant was removed from both tubes, and the contents of both tubes were washed with normal saline solution.

Both specimens thus treated, and a third untreated specimen from the same unit of platelets, were then prepared on slides and inspected as to platelet morphology. There were no differences in platelet morphology as between any of the three specimens.

5. PLASMA-PROTEIN SURVIVAL

Fresh peripheral blood was drawn from a healthy donor, and immediately centrifuged to separate cells and plasma. The plasma was drawn off in such a manner as to avoid taking any blood cells with the plasma.

Seven-and-a-half milliliters of this plasma were identified as the experimental sample to be treated. A control aliquot of two milliliters of the same plasma was set aside, and left untreated, for later analysis with the experimental sample.

A disinfectant solution was prepared as follows. First, 15.1% lactic acid, one volume, was added to ten volumes of normal saline; and to this was added a solution of 2.73% sodium chlorite in a volume equal to that of the lactic acid. Next, this combined solution was incubated at room temperature for seventy-five minutes, after which the solution was diluted 1:20 in normal saline.

Seven-and-a-half milliliters of this solution was then mixed with the experimental plasma sample, of equal volume. The mixture was then incubated at room temperature for five minutes.

Plasma proteins were then precipitated by the addition of 3.75 milliliters of saturated ammonium sulfate, at pH 7.4. The entire solution, at the time of addition, was kept on ice to maintain its temperature at four degrees Celsius.

All the material was then centrifuged. Centrifugation proceeded at 13,000 gravities for ten minutes.

The precipitated proteins were then resuspended in 7.5 milliliters of normal saline, and transferred to a semipermeable dialysis bag for dialysis against six liters of normal saline for twelve hours, in the cold room. The latter was changed three times over the twelve-hour period to remove traces of the ammonium sulfate.

Standard serum protein electrophoresis of both the treated plasma experimental sample and the untreated plasma control aliquot was then carried out by a recognized clinical immunology laboratory.

The electrophoresis alpha-1, beta and gamma peaks showed no loss of protein due to the sterilization treatment. There was, however, roughly fifty-percent loss of albumin.

Albumin loss was likely due to incomplete recovery in the precipitation and centrifugation steps, rather than damage by the sterilant solution. Longer centrifugation or addition of more ammonium sulfate would probably result in a full recovery, as demonstrated for the other, larger proteins.

6. CORNEAL-TISSUE SURVIVAL

In a preliminary test, a human cornea was immersed for fifteen seconds in a disinfectant solution prepared generally as described above for platelets, and in particular with a 1:200 dilution. The cornea was then rinsed in normal saline.

Visual microscopic examination of the corneal endothelium showed that there had been no significant change.

It will be understood that the foregoing disclosure is intended to be merely exemplary, and not to limit the scope of the invention—which is to be determined by reference to the appended claims.

I claim:

1. A method for treating a blood product comprising a quantity of at least one cellular blood constituent to inactivate or greatly reduce the activity, in the quantity of the blood constituent, of a harmful substance, said method comprising the steps of:

mixing the blood product with a disinfectant composition consisting essentially of chlorine dioxide in a solution of normal saline; and thereafter separating the chlorine dioxide from the cellular blood constituent.

2. The method of claim 1, further comprising the step of:

between the exposing step and the removing step, maintaining the disinfectant in contact with the product for a time period between approximately two-tenths minute and five minutes.

3. The method of claim 1, also comprising the step of:

before the separating step, removing the at least one blood constituent from another part of the blood product.

4. The method of claim 3, wherein:

the removing step is performed before the mixing step.

5. The method of claim 1, wherein:

the separating step comprises washing the red blood cells in normal saline.

6. A method for reducing the infectivity of a virus, to prepare a blood product for beneficial use; said method comprising the steps of:

selecting or preparing a disinfectant that comprises an acid, a water soluble chlorine dioxide liberating compound, and normal saline;

exposing a blood product, comprising at least one blood constituent selected from the group consisting of red blood cells, platelets and plasma, to the disinfectant for a time period sufficient to inactivate any of such virus that may be present;

then separating the disinfectant from the blood constituent; and then providing the blood constituent for a beneficial use.

7. The method of claim 6, wherein:

the separating step comprises washing the constituent, with normal saline, until the concentration of disinfectant is insignificant.

8. The method of claim 6, for use with a blood product that comprises plasma; wherein:

the separating step comprises precipitating out the plasma proteins.

9. The method of claim 8 wherein:

the separating step comprises precipitating out the plasma proteins with ammonium sulfate.

10. The method of claim 8 wherein:

the separating step comprises precipitating out the plasma proteins with eighty-percent or less ammonium sulfate.

11. The method of claim 8, wherein:

the separating step further comprises resuspending the plasma proteins.

12. The method of claim 8, wherein:

the separating step further comprises resuspending the plasma proteins in a small volume of normal saline, and is followed by dialyzing them exhaustively at a semipermeable membrane against a large volume of normal saline.

13. The method of claim 6, wherein:

the acid is an organic acid selected from the group consisting of monocarboxylic acids and polycarboxylic acids containing from 2 to about 16 carbon atoms.

14. The method of claim 13 wherein:

the organic acid is selected from the group consisting of lactic acid, acetic acid, sorbic acid, fumaric acid and tannic acid.

15. The method of claim 6, wherein: the acid is an inorganic acid selected from the group consisting of hydrochloric acid, sulfuric acid, and phosphoric acid.

16. The method of claim 6 wherein the organic acid is at least 15% lactic acid.

17. The method of claim 6 wherein the acid is lactic acid.

18. The method of claim 6 wherein the chlorine dioxide liberating compound is sodium chlorite.

19. The method of claim 6 wherein the chlorine dioxide liberating compound is the water soluble chlorite of an alkali earth metal.

20. The method of claim 6 wherein the acid is an inorganic acid selected from the group consisting of hydrochloric acid, sulfuric acid, and phosphoric acid.

21. The method of claim 6 wherein the acid is an organic acid selected from the group consisting of monocarboxylic acids and polycarboxylic acids containing from 2 to about 16 carbon atoms.

22. The method of claim 21 wherein the organic acid is selected from the group consisting of lactic acid, acetic acid, citric acid, sorbic acid, fumaric acid and tannic acid.

23. The method of claim 6 wherein the acid is at least 15% lactic acid.

24. The method of claim 6 wherein the acid is lactic acid.

25. A method for treating corneal or scleral tissue, to inactivate or greatly reduce the activity, in the tissue, of a virus; said method comprising the steps of:

selecting or preparing a disinfectant, said disinfectant comprising lactic acid and sodium chlorite in a normal saline solution;

exposing the corneal or sclearal tissue to the disinfectant;

thereafter separating the disinfectant from the corneal or scleral tissue; and thereafter providing the corneal or scleral tissue for use as a transplant.

26. The method of claim 25, wherein:

the exposing step comprises maintaining the disinfectant in contact with the corneal or scleral tissue for a time period less than approximately five minutes.

27. The method of claim 25 wherein the concentration of sodium chlorite is about 0.23% and the concentration of lactic acid is from about 1.1% to about 1.26%.

28. The method of claim 27 wherein the disinfectant is diluted with a normal saline solution by from about 1:2 to about 1:2000.

29. A method for treating a blood product comprising at least one cellular blood constituent, to inactivate or greatly reduce the activity of a harmful substance in the blood product, comprising the steps of:

exposing the blood product to a disinfectant, said disinfectant consisting essentially of a normal saline solution of lactic acid and sodium chlorite;

separating the disinfectant from the cellular blood produce until the disinfectant is substantially removed; and thereafter providing the blood product for beneficial use.

30. The method of claim 29 wherein the concentration of lactic acid is 1.26% and the concentration of sodium chlorite is 0.23%.

31. The method of claim 30 wherein the lactic acid and sodium chlorite is further diluted from about 1:2 to about 1:2000 in normal saline.

32. The method of claim 29 wherein the exposing step and the separating step are performed in an automated cell washer.

33. The method of claim 29 wherein the exposing step is for between about five seconds and thirty minutes.

34. A method for treating corneal or scleral tissue, to inactivate or greatly reduce the activity, in said tissue, of a virus, said method comprising the steps of:
   selecting or preparing a disinfectant, said disinfectant comprising an acid, and a chlorine dioxide liberating compound, in normal saline;
   exposing said corneal or scleral tissue to said disinfectant;
   thereafter providing said corneal or scleral tissue for use as a transplant.

* * * * *